United States Patent [19]

Ferguson

[11] Patent Number: 4,529,413
[45] Date of Patent: Jul. 16, 1985

[54] RECOVERING DESSICANT-ANTIFREEZE FROM ADMIXTURE WITH WATER AND HYDROGEN SULFIDE

[75] Inventor: Robert G. Ferguson, Bartlesville, Okla.

[73] Assignee: Phillips Petroleum Company, Bartlesville, Okla.

[21] Appl. No.: 590,826

[22] Filed: Mar. 19, 1984

[51] Int. Cl.³ .............................................. B01D 53/14
[52] U.S. Cl. ......................................... 55/32; 55/47; 55/48; 55/73; 62/20; 62/23; 203/49
[58] Field of Search .................. 55/32, 46, 48, 51, 73, 55/68, 47; 62/20, 23, 28; 203/49

[56] References Cited

U.S. PATENT DOCUMENTS

| | | | |
|---|---|---|---|
| 3,348,601 | 10/1967 | Hill | 55/32 X |
| 3,362,133 | 1/1968 | Kutsher et al. | 55/48 |
| 3,824,766 | 7/1974 | Valentine et al. | 55/48 |
| 3,886,757 | 6/1975 | McClintock et al. | 55/31 X |
| 4,014,667 | 3/1977 | Barber | 55/32 |
| 4,372,925 | 2/1983 | Cornelisse | 55/73 X |

*Primary Examiner*—Charles Hart
*Attorney, Agent or Firm*—Charles F. Steininger

[57] ABSTRACT

A mixture of a dessicant-antifreeze, water and significant amounts of hydrogen sulfide is fractionated to produce a first vapor phase predominating in dessicant-antifreeze and hydrogen sulfide and a first liquid phase of essentially purified water and the first vapor phase is contacted with a stripping gas, inert with respect to the dessicant-antifreeze, to produce a second gas phase predominating in stripping gas and the hydrogen sulfide and a liquid phase of essentially purified dessicant-antifreeze. The first gas phase is preferably cooled and separated into the third liquid phase predominating in dessicant-antifreeze and a third vapor phase containing the remainder of the hydrogen sulfide and the third liquid phase is utilized as the feed to the stripping step. In the latter embodiment the second and third gas phases are combined and utilized as previously indicated. A method for dehydrating a natural gas stream containing significant amounts of hydrogen sulfide is also disclosed in which the natural gas is contacted with an aqueous dessicant-antifreeze to produce a gas phase containing most of the hydrocarbons and hydrogen sulfide and a liquid phase containing the dessicant-antifreeze and water and, after separating a gas predominating in methane and a vapor phase predominating in $C_2^+$ hydrocarbons, the mixtures of water, dessicant-antifreeze and hydrogen sulfide is treated as above.

20 Claims, 1 Drawing Figure

RECOVERING DESSICANT-ANTIFREEZE FROM ADMIXTURE WITH WATER AND HYDROGEN SULFIDE

The present invention relates to a method of recovering dessicant-antifreeze from a liquid stream comprising the dessicant-antifreeze, water and significant amounts of hydrogen sulfide. A still further object of the present invention is to provide an improved method for the recovery of essentially pure dessicant-antifreeze from a liquid stream comprising said dessicant-antifreeze, water and significant amounts of hydrogen sulfide and this method in combination with reducing the moisture content of natural gas.

BACKGROUND OF THE INVENTION

It is known in the art to refrigerate natural gas streams to facilitate the separation of impurities therefrom, to facilitate the separation of various components of the gas and to liquify the gas for storage and shipment. For example, it is common practice to refrigerate a natural gas stream to a temperature low enough to condense hydrocarbons heavier than methane. The liquified heavier hydrocarbons are then readily separated from the gas predominating in methane. One problem in reducing the temperature of a natural gas stream below 32° F. is the condensation of water vapor usually contained therein, with the resultant freezing thereof to form ice crystals and/or water-hydrocarbon hydrate crystals. In fact, water-hydrocarbon hydrate crystals are usually formed at temperatures above 32° F. sometimes as high as 40° F. Such ice crystals and hydrates tend to plug the heat exchangers in the chilling or cooling stage and make operation thereof impossible for a short time. Carbon dioxide and hydrogen sulfide, if present in the gas, will also freeze out of the gas if it is cooled to a temperature in the order of about $-115°$ F.

In order to overcome the above-mentioned formation of ice crystals and solid hydrates in natural gas processing systems, the water and carbon dioxide are removed to the extent possible before the natural gas feedstock is cooled below the temperature at which such solids will form. One method to accomplish this comprises contacting the gas with a high boiling (low vapor pressure) liquid dessicant, such as diethylene glycol or triethylene glycol, to absorb the water. High boiling dessicants are used in such processes so as to minimize introduction of the dessicant into the gas stream by evaporation. Such processes have the disadvantage of high operating costs, particularly in the recovery of the dessicant. In addition, glycols become very viscous at low temperatures and present a handling problem in and of themselves. Another method which has been employed is to pass the gas through towers containing solid adsorbents, such as silica gel, molecular sieve, solid caustic, etc. Such adsorbents and the operating costs associated therewith are expensive. Because of the expense of such operations, cheaper solutions to the problems have been sought. More recently, an antifreeze such as methyl alcohol has been added to the natural gas feedstock and passed together with the feedstock through low temperature heat exchange units. As the water is condensed from the gas, it is absorbed by the alcohol to form a liquid alcohol-water phase which separates from the gaseous feedstock being cooled. While, in general, this process has been more economical than the use of adsorbing dessicants, the process is not without problems. For example, when heavier hydrocarbons condense from the natural gas in contact with the alcohol-water phase, two liquid phases are present in the equipment, a hydrocarbon phase and a water-alcohol phase. Since the alcohol is also soluble in the hydrocarbon phase, it may transfer from the water phase to the larger volume hydrocarbon phase leaving insufficient alcohol in the water phase which will then freeze and plug the equipment.

In order to alleviate the above-mentioned problems, it has been common practice to contact the natural gas with an aqueous liquid dessicant-antifreeze agent in a manner to remove at least a portion of the moisture contained in the gas and introduce a sufficient amount of the dessicant-antifreeze in the vapor phase into the gas so as to prevent formation of solids in subsequent low temperature treating steps. Further improvement is obtained by separating the aqueous, dessicant-antifreeze from the gas and other hydrocarbons being treated and then fractionate the water and dessicant-antifreeze mixture to separate water therefrom and thus adjust the water content of the aqueous solution utilized to treat the gas for recycle to the gas contacting step.

While the above-mentioned recovery of water and dessicant-antifreeze for reuse is effective where the dessicant-antifreeze contains only water, serious problems exist when the water and dessicant-antifreeze contains other impurities. For example, hydrogen sulfide, if present in significant amounts in the natural gas being treated, will concentrate in the dessicant-antifreeze phase in the fractionator. Because of this, the dessicant-antifreeze is unacceptable for reuse and must be disposed of. While heat stripping of the hydrogen sulfide from the dessicant-antifreeze can be utilized to purify the dessicant-antifreeze, such an operation involves substantial investments operating costs and results in significant losses of the dessicant-antifreeze. In addition, such heat stripping produces a gaseous phase containing the hydrogen sulfide which is normally vented to the atmosphere and, of course, causes undesirable pollution problems.

SUMMARY OF THE INVENTION

It is an object of the present invention to provide an improved method for recovering dessicant-antifreeze which overcomes the above-mentioned and other problems of the prior art. Another object of the present invention is to provide an improved method for recovering purified dessicant-antifreeze from a liquid comprising the dessicant-antifreeze, water and significant amounts of hydrogen sulfide. A further object of the present invention is to provide an improved method for the recovery of purified dessicant-antifreeze from a liquid mixture of dessicant-antifreeze, water and significant amounts of hydrogen sulfide, which produces a dessicant-antifreeze suitable for reuse. Another and further object of the present invention is to provide an improved method for recovering purified dessicant-antifreeze from a liquid mixture of dessicant-antifreeze, water and significant amounts of hydrogen sulfide, which produces a dessicant-antifreeze suitable for reuse and additionally makes it unnecessary to vent or flare a gas stream containing hydrogen sulfide. Yet another object of the present invention is to provide an improved method for recovering purified dessicant-antifreeze from a liquid mixture comprising dessicant-antifreeze, water and significant amounts of hydrogen sulfide, in accordance with the next previous object, in which the hydrogen sulfide is recovered in a usable form. Another and further object of the present invention is to provide an improved method for recovering purified dessicant-antifreeze from a liquid stream comprising dessicant-antifreeze, water and significant amounts of hydrogen sulfide which is economical to install and operate. A further object of the present invention is to provide an improved method of recovering purified dessicant-antifreeze from a liquid stream comprising dessicant-antifreeze, water and significant amounts of hydrogen sulfide, comprising; a simple and economical two-step process. Another object of the present invention is to provide an improved method for reducing the moisture content of a natural gas stream containing significant amounts of moisture and hydrogen sulfide, including; contacting the natural gas with a dessicant-antifreeze, separating a dessicant-antifreeze, water and hydrogen sulfide mixture from the hydrocarbons and recovering essentially purified dessicant-antifreeze from said mixture.

In accordance with the present invention, essentially pure dessicant-antifreeze is recovered from a liquid mixture of dessicant-antifreeze, water and significant amounts of hydrogen sulfide by fractionating the liquid stream under conditions and in a manner to produce a vapor phase predominating in dessicant-antifreeze and hydrogen sulfide and a liquid phase comprising essentially purified water and contacting the vapor phase with a stripping gas, essentially inert with respect to the dessicant-antifreeze, under conditions and in a manner to produce a gas phase predominating in the stripping gas and hydrogen sulfide and a liquid phase comprising essentially purified dessicant-antifreeze.

BRIEF DESCRIPTION OF THE DRAWING

The drawing shows a simplified flow diagram of a natural gas dehydrating system, including the system of the present invention.

DESCRIPTION OF PREFERRED EMBODIMENTS

Figure 1:
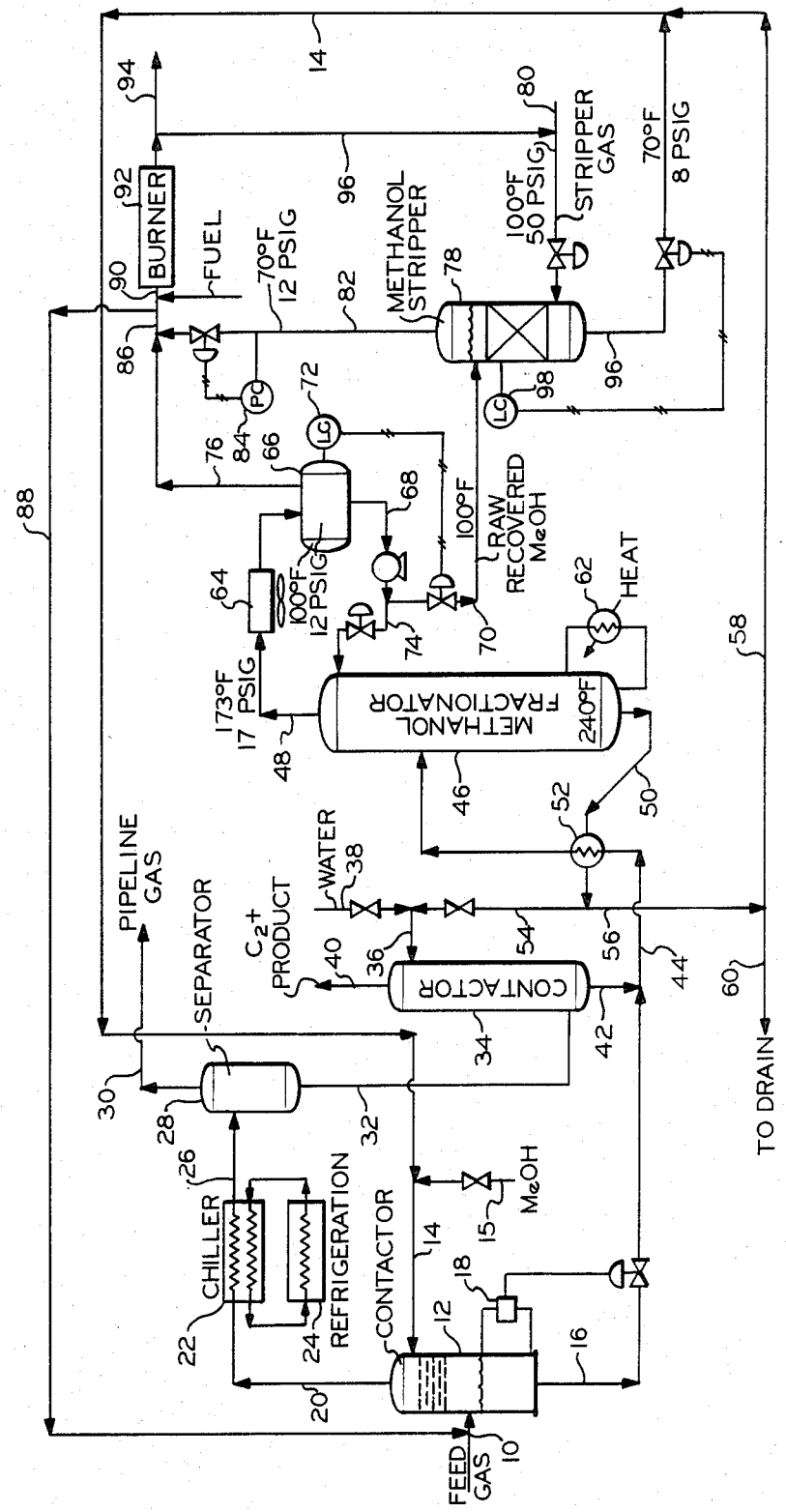

The nature of the present invention and its advantages can be best illustrated and its advantages set forth by reference to a preferred embodiment of the invention, as shown in the single figure of drawings. Since, in accordance with the present invention, a preferred dessicant-antifreeze agent is methanol, the detailed description, when read in conjunction with the drawings, will make reference to such use of methanol.

A natural gas feed predominating in methane and containing relatively small amounts of ethane, propane, butanes and heavier hydrocarbons, as well as significant amounts of moisture and hydrogen sulfide is introduced to the system through line 10. Such a gas stream will normally be at atmospheric temperature and at an elevated pressure, either as it is produced or after compression. For example, a typical has would be at a pressure of about 550 psig and about 80° F. The natural gas feed is introduced into the lower portion of a gas-liquid contactor 12 where it passes upwardly through the contacting trays shown, countercurrently to a descending stream of dehydrating agent, i.e., aqueous methanol introduced through line 14. Make-up methanol may be added as needed through line 15. About 2 to 6 trays of conventional design, for example bubble cap or sieve, are usually sufficient for the contacting to thus produce a treated gas containing reduced amounts of water. The resulting water-methanol solution is removed from contactor 12 through line 16. Discharge of the water-methanol solution may be controlled by a level controller such as 18 and passed to a methanol recovery operation, as described hereinafter.

The treated gas stream is discharged from contactor 12 through line 20 and introduced into chiller zone 22 where it is cooled by heat exchange with a cold refrigerant fluid produced by refrigeration unit 24. Such cooling is sufficient to condense ethane and heavier hydrocarbons from the bas. The chilled gas stream is withdrawn from chiller 22 by way of conduit 16 and introduced into phase separator 28. Non-liquified gas comprising essentially methane, together with small amounts of ethane is withdrawn from separator 28 through line 30 and is suitable for use as a pipeline gas. A liquid phase from separator 28 comprising $C_2$ and heavier hydrocarbons, as well as essentially all of the methanol, water and hydrogen sulfide is withdrawn through line 32. The liquid stream from line 32 is countercurrently contacted in liquid-liquid contactor 34 with a descending stream of water introduced through line 36, preferably obtained from a source hereinafter described. However, water from an outside source may be introduced through line 38. Contactor 34 may be operated in any suitable temperature, for example within the range of about 40° F. to about 125° F., and at any suitable pressure, for example within the range of from about 10 to about 500 psig, to maintain both the water and the hydrocarbon phases in a preferred liquid state. The descending water extracts essentially all of the methanol and hydrogen sulfide from the condensed hydrocarbons and produces an essentially alcohol-free product comprising $C_2$ and heavier hydrocarbons which is withdrawn through line 40. The $C_2$ and heavier hydrocarbon product can be further processed in accordance with conventional practice to separate the individual components for example, ethane, propane, butanes and $C_5$ and heavier hydrocarbons. An alternative not shown would be to introduce both the gas phase from separator 28 and the liquid phase from separator 28 to a demethanizer or fractionating column, at appropriate different elevations in the column, wherein the mixture is separated into a gas stream comprising principally methane, a $C_2$ and higher hydrocarbon stream and a liquid stream comprising substantially all of the methanol, the water and the hydrogen sulfide. The latter stream would then be fed to liquid liquid-contactor 34. The bottoms or liquid phase from contactor 34 comprises essentially all of the methanol, water and hydrogen sulfide and is withdrawn through line 42.

The mixtures of methanol, water and hydrogen sulfide passing through lines 16 and 42, respectively, are combined in line 44 and fed to methanol fractionator 46. In methanol fractionator 46, the mixture is fractionated, at a bottom temperature of about 240° F., to produce an overhead stream comprising essentially all of the methanol and hydrogen sulfide which is withdrawn through line 48. This overhead would, for example, be at a temperature of about 173° F. and a pressure of about 17 psig. The liquid bottoms product from fractionator 46 comprises substantially all of the water and a small amount of methanol but is substantially free of hydrocarbons and hydrogen sulfide. This water stream may be withdrawn through line 50 and passed through indirect heat exchanger 52 to heat the feed stream to fractionator 46 passing through line 44. Thereafter, the essentially purified water is recycled to contactor 34 by way of line 54. Alternatively, at least a portion of the water can be passed through line 56 and line 58 and thus recycled to join the aqueous methanol to contactor 12 through line 14. Excess water not necessary for use in contactor 12 or contactor 46 may be discharged through line 60. Since this water is substantially free of hydrocarbons, methanol and hydrogen sulfide, it may be passed to a drain without danger of pollution. Additional heat, as necessary, is provided to fractionator 46 by heater 62. The gas phase from fractionator 46, comprising essentially all of the methanol, all of the hydrogen sulfide and residual hydrocarbons and withdrawn through line 48, is preferably cooled, as by an atmospheric tower or the like, in cooling unit 64. Such cooling is selected to condense a methanol phase containing a substantial volume of the hydrogen sulfide from a gas phase comprising hydrogen sulfide and some methanol in condensor 66. The methanol containing significant amounts of hydrogen sulfide and some water is withdrawn through lines 68 and 70. Discharge of liquid from condensor 66 is preferably controlled by means of level controller 72. A part of the liquid methanol containing significant amounts of hydrogen sulfide may also be fed through line 74 to the top of fractionator 46 as a reflux. The gas phase from condensor 66 is withdrawn through line 76. This gas phase will contain hydrogen sulfide and small amounts of vaporized methanol. As previously indicated, it has been conventional practice to vent this gas phase to the atmosphere or burn it in a flare and discharge the same to the atmosphere. In any event, such discharge to the atmosphere creates a serious pollution problem. Raw recovered methanol at a temperature of about 100° F passing through line 70 is introduced into methanol stripper 78. In methanol stripper 78, the raw methanol is countercurrently contacted with a stripper gas introduced through line 80. The stripper gas may appropriately be any inert gas or gas which is essentially inert with respect to the methanol. The stripping gas is introduced at a temperature of about 100° F. and a pressure of about 50 psig. Suitable gases include a flue gas from a process heater or other combustor or burner within the plant itself or may be a low Btu fuel gas. In stripper 78, the stripper gas removed substantially all of the hydrogen sulfide from the raw methanol and discharges the same as a gas phase through line 82 at a temperature of about atmospheric temperature (about 70° F.) and a pressure of about 12 psig. Discharge of this gas phase may be controlled by means of pressure controller 84. Normally, in conventional operations, such a gas would be vented to the atmosphere or flared. However, in accordance with the present invention, the gas phase from methanol stripper 78, comprising the stripper gas and substantially all of the hydrogen sulfide and passing through line 82, is combined with the gas phase from condensor 66, passing through line 76, and passed to line 86. From line 86, several alternatives for use of the gas are possible. In a preferred embodiment, this gas phase is passed through line 88 and recycled to the natural gas stream being fed to the dehydration system. Alternatively, since this gas may contain some combustibles, all or a part thereof may be passed through line 90 to an appropriate burner or combustor 92, preferably an in-plant burner or combuster such as heater 62. The flue gas from burner 92 may be vented in conventional manner through line 94 or all or a part thereof may be utilized as a stripping gas by passing the same through line 96 to methanol stripper 78. To the extent that it is desired to burn the gas phase from condenser 66 and methanol stripper 78, additional fuel gas may be introduced through line 80 from an outside source. Liquid bottoms product for methanol stripper 78, comprising essentially purified methanol substantially free of hydrocarbons and hydrogen sulfide is withdrawn through line 96 and in such purified state is suitable for reuse in the dehydration process and, therefore, is introduced into line 14 for recycle to contactor 12. As previously indicated, methanol contaminated with hydrogen sulfide is conventionally disposed of, since it is of insufficient purity for reuse. Obviously such disposal is not only expensive but creates pollution problems of its own. Discharge of purified methanol through line 96 can be appropriately controlled by means of level controller 98.

In order to illustrate the advantages of the present invention, a material balance has been calculated, which calculated values closely approximate the values of an actual plant which has been built in accordance with the present invention. The material balance, as indicated in the following table, is based on pounds per day of the specified components and the line references are to the lines of the drawing.

| MATERIAL BALANCE | | | | | | | | |
|---|---|---|---|---|---|---|---|---|
| Basis: Pounds per day | | | | | | | | |
| Line | 44 | 50 | 76 | 70 | 80 | 82 | 86 | 96 |
| MeOH | 8,553 | 564 | 58 | 7,931 | | 89 | 147 | 7,842 |
| H$_2$O | 143,942 | 143,521 | | 421 | | | | 421 |
| H$_2$S | 469 | | 290 | 179 | | 179 | 469 | Nil |
| C$_1$ | | | | | 408 | 408 | 408 | |
| C$_2^+$ | | | | | 144 | 144 | 144 | |
| | 152,964 | 144,085 | 348 | 8,531 | 552 | 820 | 1,168 | 8,263 |

It is to be observed from the above Table that the water from methane fractionator 46 is substantially pure and contains only extremely small amounts of methanol and immeasurable amounts of hydrocarbons. The gas phase from condensor 66 contains a major portion of the hydrogen sulfide, together with small amounts of methanol. The raw methanol stream from fractionator 46 and condensor 66 predominates in methanol and contains small amounts of water and less than half, but significant amounts, of hydrogen sulfide. The gas phase from methanol stripper 78 contains substantially all of the hydrocarbons in the stripping gas, substantially all of the hydrogen sulfide, which still contaminates the methanol from fractionator 46, and small amounts of methanol. The combined gas phases from condensor 66 and stripper 78 contain all of the stripper gas, substantially all of the hydrogen sulfide originally present in the methanol, water and hydrogen sulfide mixture and a small amount of methanol. The purified methanol from methanol stripper 78 contains substantially all of the methanol, a small amount of water and insignificant amounts of hydrogen sulfide. Thus it is obvious that the practice of the present invention produces an essentially pure methanol stream for reuse in dehydrating gas, a substantially purified water stream for reuse with the methanol in dehydrating the gas or for use in separating ethane and heavier hydrocarbons from the methanol-water-hydrogen sulfide mixture or which can be disposed of in a conventional drain. The practice of the present invention also produces an effluent gas phase containing substantially all of the hydrogen sulfide which can be recycled to the natural gas feed to the dehydration plant or burned as a low Btu fuel.

While the present invention has been described with reference to specific items of equipment, modes of oper- That which is claimed:

1. A method of producing a mixture of a purified dessicant-antifreeze, having a boiling point below the boiling point of water, and a purified water, having a predetermined ratio of dessicant-antifreeze to water, from an impure liquid stream comprising said dessicant-antifreeze, water and hydrogen sulfide, comprising:

(a) fractionating said liquid stream under conditions and in a manner to produce a first vapor phase predominating in said dessicant-antifreeze and said hydrogen sulfide and a first liquid phase of essentially purified water;

(b) condensing said first vapor phase to produce a second vapor phase and a second Liquid phase;

(c) contacting said second Liquid phase with a stripping gas, essentially inert with respect to said dessicant-antifreeze, under conditions and in a manner to produce a third vapor phase predominating in said stripping gas and said hydrogen sulfide and a third liquid phase of essentially purified dessicant-antifreeze; and (d) mixing a predetermined portion of said first liquid phase with said third liquid phase to produce said mixture of dessicant-antifreeze and water having a predetermined ratio of dessicant-antifreeze to water.

2. A method in accordance with claim 1 wherein the first vapor phase is cooled to a temperature sufficient to condense substantially all of the dessicant-antifreeze and produce a third liquid phase predominating in said dessicant-antifreeze and a portion of the hydrogen sulfide and a third gas phase containing the remainder of the hydrogen sulfide, separating said third gas phase from said third liquid phase and passing said third liquid phase as a feed to the stripping step.

3. A method in accordance with claim 2 wherein the second gas phase is combined with the third gas phase.

4. A method in accordance with claim 3 wherein the combined second gas phase and third gas phase are burned as an in-plant fuel.

5. A method in accordance with claim 1 wherein the dessicant-antifreeze is methanol.

6. A method in accordance with claim 1 wherein the stripping gas is flue gas.

7. A method in accordance with claim 1 wherein the stripping gas is a fuel gas.

8. A method in accordance with claim 7 wherein the second gas phase is burned as an in-plant fuel.

9. A method in accordance with claim 1 wherein the second gas phase is burned as an in-plant fuel.

10. A method for reducing the moisture content of a natural gas stream containing significant amounts of hydrocarbons heavier than methane, moisture and hydrogen sulfide, comprising:

(a) contacting said natural gas with an aqueous liquid solution of a dessicant-antifreeze, having a boiling point below the boiling point of water, to absorb said moisture and produce a treated first vapor phase and a first liquid phase comprising water and said dessicant-antifreeze;

(b) separating the thus treated first vapor phase into a second vapor phase rich in methane and a second liquid phase predominating in said hydrocarbons heavier than methane, said dessicant-antifreeze, water and said hydrogen sulfide;

(c) fractionating said second liquid phase to separate a third vapor phase rich in said hydrocarbons heavier than methane and a third liquid phase predominating in said dessicant-antifreeze, water and said hydrogen sulfide;

(d) fractionating said first liquid phase and said third liquid phase, under conditions and in a manner to produce a fourth vapor phase predominating in said dessicant-antifreeze and said hydrogen sulfide and a fourth liquid phase of essentially purified water;

(e) condensing said forth vapor phase to produce a fifth vapor phase and a fifth liquid phase;

(f) contacting said fifth liquid phase with a stripping gas, essentially inert with respect to said dessicant-antifreeze, under conditions and in a manner to produce a sixth vapor phase predominating in said stripping gas and said hydrogen sulfide and a sixth liquid phase of essentially purified dessicant-antifreeze;

(g) adding at least a portion of said fourth liquid phase to said sixth liquid phase to produce a mixture of dessicant-antifreeze and water; and (h) recycling said mixture of dessicant-antifreeze and water to step (a) as at least a part of said aqueous liquid solution of dessicant-antifreeze.

11. A method in accordance with claim 10 wherein a predetermined portion of the fourth liquid phase is added to the fifth liquid phase in accordance with step (g) to produce the mixture of dessicant-antifreeze and water, having a predetermined ratio of dessicant-antifreeze to water.

12. A method in accordance with claim 10 wherin the fourth vapor phase is cooled to a temperature sufficient to condense substantially all of the dessicant-antifreeze and produce a sixth liquid phase predominating in dessicant-antifreeze and a portion of the hydrogen sulfide and a sixth vapor phase containing the remainder of the hydrogen sulfide, separating said sixth vapor phase and said sixth liquid phase and passing said sixth liquid phase as a feed to the stripping step.

13. A method in accordance with claim 12 wherein the sixth vapor phase is combined with the fifth vapor phase.

14. A method in accordance with claim 13 wherein the combined sixth vapor phase and fifth vapor phase are recycled to the natural gas feed to the system.

15. A method in accordance with claim 14 wherein the combined sixth vapor phase and fifth vapor phase are burned as an in-plant fuel.

16. A method in accordance with claim 10 wherein the dessicant-antifreeze is methanol.

17. A method in accordance with claim 10 wherein the stripping gas is a flue gas.

18. A method in accordance with claim 10 wherein the stripping gas is a fuel gas.

19. A method in accordance with claim 18 wherein the fifth vapor phase is burned as an in-plant fuel.

20. A method in accordance with claim 10 wherein the fifth vapor phase is recycled to the natural gas feed to the system.

* * * * *